(12) United States Patent
Keller

(10) Patent No.: US 11,246,992 B2
(45) Date of Patent: Feb. 15, 2022

(54) SELF-ADMINISTRATIVE MEDICAMENT DEVICE CONFIGURED TO SEND DATA THROUGH THE HUMAN BODY

(71) Applicant: Carebay Europe Ltd., Sliema (MT)

(72) Inventor: Christian Keller, Taipei (TW)

(73) Assignee: SHL MEDICAL AG, Zug (CH)

( * ) Notice: Subject to any disclaimer, the term of this patent is extended or adjusted under 35 U.S.C. 154(b) by 130 days.

(21) Appl. No.: 16/341,425

(22) PCT Filed: Sep. 15, 2017

(86) PCT No.: PCT/EP2017/073348
§ 371 (c)(1),
(2) Date: Apr. 11, 2019

(87) PCT Pub. No.: WO2018/068986
PCT Pub. Date: Apr. 19, 2018

(65) Prior Publication Data
US 2020/0038593 A1 Feb. 6, 2020

(30) Foreign Application Priority Data

Oct. 14, 2016 (EP) .................................. 16193937

(51) Int. Cl.
*A61M 5/315* (2006.01)
*A61B 5/0531* (2021.01)
(Continued)

(52) U.S. Cl.
CPC ......... *A61M 5/3158* (2013.01); *A61B 5/0531* (2013.01); *A61B 18/14* (2013.01);
(Continued)

(58) Field of Classification Search
CPC ...... A61M 5/3158; A61M 5/20; A61M 15/00; A61M 2005/2013; A61M 2205/3538;
(Continued)

(56) References Cited

U.S. PATENT DOCUMENTS 8,939,928 B2   1/2015   Savoie et al.
2011/0022025 A1*  1/2011  Savoie ................ H04B 13/005
                                                   604/500
(Continued)

FOREIGN PATENT DOCUMENTS

CN       104853788 A    8/2015
EP       2722065 A1    4/2014
(Continued)

OTHER PUBLICATIONS

English Translation of Search Report issued in Taiwanese Patent Application No. 106132941 dated Nov. 9, 2018.

*Primary Examiner* — Bhisma Mehta
*Assistant Examiner* — Robert F Allen
(74) *Attorney, Agent, or Firm* — McDonnell Boehnen Hulbert & Berghoff LLP

(57) ABSTRACT

The present disclosure relates to a self-administrative medicament device (1) comprising: processing circuitry (3), a transmitter (9) having a first electrode (7*a*) configured to be coupled to a user's skin, a power supply system (11) configured to apply a current to the transmitter, and a trigger member (7) configured to trigger the power supply to apply the current to the transmitter (9), wherein the processing circuitry (3) is configured to modulate the current generated by the power supply system (11) to encode medicament administration-related data to be transmitted through a user's skin by the transmitter (9) via the first electrode (9*a*).

15 Claims, 5 Drawing Sheets

(51) Int. Cl.
*A61B 18/14* (2006.01)
*A61M 5/20* (2006.01)
*A61M 15/00* (2006.01)

(52) U.S. Cl.
CPC .............. *A61M 5/20* (2013.01); *A61M 15/00* (2013.01); *A61M 2005/2013* (2013.01); *A61M 2205/3538* (2013.01); *A61M 2205/3553* (2013.01); *A61M 2205/52* (2013.01)

(58) Field of Classification Search
CPC ...... A61M 2205/3553; A61M 2205/52; A61M 2205/3561; A61M 2205/3584; A61M 2205/505; A61M 2205/3569; A61M 2205/50; A61M 5/3202; A61B 5/0531; A61B 18/14; H04B 13/005
See application file for complete search history.

(56) References Cited

U.S. PATENT DOCUMENTS

| | | |
|---|---|---|
| 2011/0156908 A1 | 6/2011 | Sekine |
| 2014/0272861 A1 | 9/2014 | Bergman et al. |
| 2015/0246176 A1* | 9/2015 | Navarro ............ A61M 5/14248 604/506 |
| 2016/0012205 A1* | 1/2016 | Saint ........................ H04B 7/24 604/154 |
| 2016/0166768 A1 | 6/2016 | Edwards et al. |
| 2016/0175524 A1* | 6/2016 | Henderson .......... A61M 5/3204 604/506 |
| 2016/0243318 A1 | 8/2016 | Despa et al. |
| 2017/0164881 A1* | 6/2017 | Fujita .................. A61B 5/1451 |

FOREIGN PATENT DOCUMENTS

| | | | |
|---|---|---|---|
| WO | 2008002821 A1 | 1/2008 | |
| WO | 2015091602 A1 | 6/2015 | |
| WO | WO-2015091602 A1 * | 6/2015 | ............. G16H 20/10 |
| WO | 2016033496 A1 | 3/2016 | |
| WO | WO-2016033496 A1 * | 3/2016 | .......... A61M 5/3234 |
| WO | WO-2017108272 A1 * | 6/2017 | .......... A61M 5/5086 |

* cited by examiner

SELF-ADMINISTRATIVE MEDICAMENT DEVICE CONFIGURED TO SEND DATA THROUGH THE HUMAN BODY

CROSS REFERENCE TO RELATED APPLICATIONS

The present application is a U.S. National Phase Application pursuant to 35 U.S.C. § 371 of International Application No. PCT/EP2017/073348 filed Sep. 15, 2017, which claims priority to European Patent Application No. 16193937.6 filed Oct. 14, 2016. The entire disclosure contents of these applications are hereby incorporated by reference into the present application.

TECHNICAL FIELD

The present disclosure generally relates to self-administrative medicament devices.

BACKGROUND

Medicament devices may utilise the body to transmit data to a host device, as disclosed in U.S. Pat. No. 8,939,928 B2. This document discloses a wearable, self-contained drug infusion or medical device capable of communicating with a host controller or other external devices via a personal area network (PAN). The medical device utilizes a PAN transceiver for communication with other devices in contact with a user's body, such as a physiological sensor or host controller, by propagating a current across the user's body via capacitive coupling. The wearable nature of the medical device and the low power requirements of the PAN communication system enable the medical device to utilize alternative energy harvesting techniques for powering the device.

The medical device disclosed in U.S. Pat. No. 8,939,928 B2 includes a pump mechanism and typically provides medicament infusion essentially continuously utilising a microprocessor.

SUMMARY

Self-administrative medicament devices, i.e. medicament devices which necessitate action by a subject to initiate a medicament administration procedure are unlike medicament device that include a pump mechanism not microprocessor-controlled. For these devices, medicament administration is mechanical in the sense that the components that initiate and provide medicament expulsion are mainly mechanical components, and their cooperation is initiated mechanically by a user.

An object of the present disclosure is to provide a self-administrative medicament device which enables data transmission through the human body.

There is hence according to a first aspect of the present disclosure provided self-administrative medicament device comprising: processing circuitry, a transmitter having a first electrode configured to be coupled to a user's skin, a power supply system configured to apply a current to the transmitter, and a trigger member configured to trigger the power supply to apply the current to the transmitter, wherein the processing circuitry is configured to modulate the current generated by the power supply system to encode medicament administration-related data to be transmitted through a user's skin by the transmitter via the first electrode.

In this manner, medicament administration-related data may be sent from a self-administrative medicament device through a user's body to a receiver without the use of antennas. The trigger member is able to initiate data transmission when a medicament administration procedure is commenced or during a medicament administration procedure.

Communication provided through the body as transmission medium is more secure compared to data transmitted wirelessly by an antenna. The data transmission procedure is triggered by movement of a movable member arranged in the self-administrative medicament device, which movement only occurs during a medicament administration procedure initiated by a user. This may also facilitate to fulfil requirements regarding compliance.

The first electrode is configured to be capacitively, galvanically or inductively coupled to a user's skin.

According to one embodiment the trigger member is configured to trigger the power supply system to apply the current to the transmitter during a medicament expulsion procedure.

One embodiment comprises a movable member configured to be moved during the medicament expulsion procedure, wherein the trigger member is configured to be actuated by the movable member to thereby trigger the power supply system.

According to one embodiment the movable member is a delivery member cover, wherein the first electrode is provided on the delivery member cover.

According to one embodiment the first electrode is provided at a proximal end surface of the delivery member cover.

One embodiment comprises a delivery member, wherein the delivery member defines the first electrode.

One embodiment comprises a housing, wherein the delivery member cover is configured to be received by the housing and to be axially displaceable between an extended position relative to the housing, in which the delivery member cover extends proximally from the housing and a retracted position, wherein the trigger member is a mechanical switch configured to be actuated by the delivery member cover when the delivery member cover is axially displaced from the extended position towards the retracted position.

According to one embodiment the power supply system includes an energy storage unit and a DC/AC converter, wherein the processing circuitry is configured to control the DC/AC converter to modulate the current to encode the medicament administration-related data.

One embodiment comprises a receiver having a second electrode configured to be coupled to a user's skin, which receiver is configured to receive the medicament administration-related data transmitted by the transmitter via the user's skin.

According to one embodiment the medicament administration-related data includes at least one of a timestamp of medicament administration, drug identification, self-administrative medicament device identification, and drug status.

According to one embodiment the self-administrative medicament device is an injector or an inhaler.

There is according to a second aspect of the present disclosure provided a medicament system comprising: a self-administrative medicament device according to the first aspect, and a portable device comprising a receiver having a second electrode configured to be coupled to a user's skin, wherein the self-administrative medicament device is configured to transmit the medicament administration-related data via the transmitter to the receiver.

The second electrode is configured to be capacitively, galvanically or inductively coupled to a user's skin.

According to one embodiment the portable device is a wearable device or a smart phone.

According to one embodiment the wearable device is a smart watch or a smart wrist band.

There is according to a third aspect provided an add-on device for a self-administrative medicament device comprising: a mechanical connector configured to connect the add-on device to a self-administrative medicament device, processing circuitry, a transmitter having a first electrode configured to directly or indirectly be coupled to a user's skin, a power supply system configured to apply a current to the transmitter, and a trigger member configured to trigger the power supply to apply the current to the transmitter, wherein the processing circuitry is configured to modulate the current to encode medicament administration-related data to be transmitted through a user's skin by the transmitter via the first electrode.

According to one embodiment the add-on device has a button configured to trigger medicament expulsion from a self-administrative medicament device, wherein the first electrode is provided on the button.

According to one embodiment the first electrode is configured to be connected to an electrode of a self-administrative medicament device.

According to one embodiment the trigger member is configured to trigger the power supply system to apply the current to the transmitter during a medicament expulsion procedure.

The first electrode is configured to be capacitively, galvanically or inductively coupled to a user's skin.

Generally, all terms used in the claims are to be interpreted according to their ordinary meaning in the technical field, unless explicitly defined otherwise herein. All references to "a/an/the element, apparatus, component, means, etc. are to be interpreted openly as referring to at least one instance of the element, apparatus, component, means, etc., unless explicitly stated otherwise.

BRIEF DESCRIPTION OF THE DRAWINGS

The specific embodiments of the inventive concept will now be described, by way of example, with reference to the accompanying drawings, in which.

DETAILED DESCRIPTION

The inventive concept will now be described more fully hereinafter with reference to the accompanying drawings, in which exemplifying embodiments are shown. The inventive concept may, however, be embodied in many different forms and should not be construed as limited to the embodiments set forth herein; rather, these embodiments are provided by way of example so that this disclosure will be thorough and complete, and will fully convey the scope of the inventive concept to those skilled in the art. Like numbers refer to like elements throughout the description.

With the term "proximal end" of a self-administrative medicament device is meant that end which is to be pointed towards the injection site during medicament injection. The same considerations also apply when referring to any component of the self-administrative medicament device. The "distal end" is the opposite end relative to the proximal end. With "proximal direction" and, equivalently, "proximally" is meant a direction from the distal end towards the proximal end, along the central axis of the self-administrative medicament device. With "distal direction" or "distally" is meant the opposite direction to "proximal direction".

The present disclosure relates to a self-administrative medicament device which comprises processing circuitry, a transmitter, a power supply system configured to apply a current to the transmitter, and a trigger member.

The transmitter has a first electrode configured to be capacitively, galvanically or inductively to the skin of a user.

The trigger member is configured to trigger the power supply to apply the current to the transmitter. In particular, the trigger member is configured to trigger the power supply system to apply the current to the transmitter during a medicament expulsion procedure. The processing circuitry is configured to modulate the current to encode medicament administration-related data to be transmitted through a user's skin via the first electrode.

Figure 1:
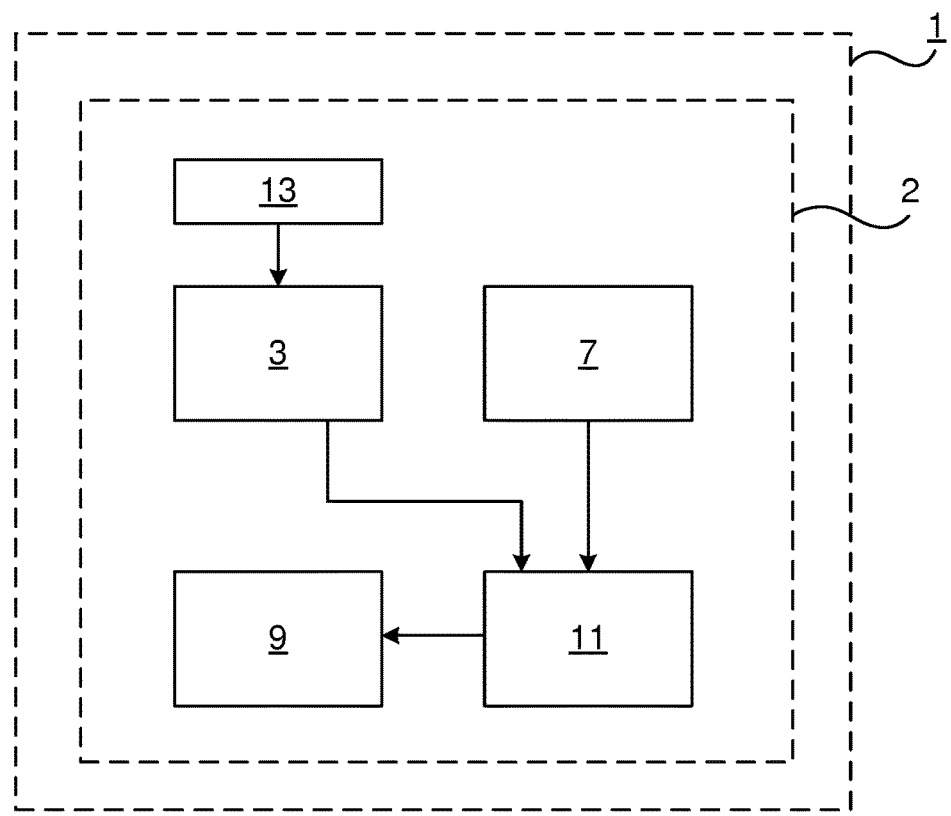
FIG. 1 schematically shows a block diagram of a general example of a self-administrative medicament device.

With reference to FIG. 1 an example of a self-administrative medicament device 1 is shown in block diagram form, to schematically illustrate electronic components thereof.

The self-administrative medicament device 1 may for example be an injector or an inhaler.

The exemplified self-administrative medicament device 1 comprises a housing configured to receive a medicament container assembly including a medicament container, and a delivery member through which medicament contained in the medicament container may be expelled. The delivery member may in the case the self-administrative medicament device 1 is an injector be a needle, and in the case it is an inhaler, be a nozzle.

The self-administrative medicament device 1 furthermore comprises processing circuitry 3, a trigger member 7, a transmitter 9 provided with a first electrode, and a power supply system 11. The trigger member 7 is configured to trigger the power supply system 11 to apply a current to the transmitter 9, and the processing circuitry 3 is configured to modulate the current to encode medicament administration-related data provided by the processing circuitry 3.

The trigger member 7 is configured to trigger the power supply system 11 to apply a current to the transmitter 9 during a medicament administration procedure. The trigger member 7, for example a mechanical switch or an optical sensor, is actuated or triggered by movement of a movable member of the self-administrative medicament device 1. The movable member is configured to be moved during a medicament administration procedure, as will be described in more detail below.

The power supply system 11 may include a DC/AC converter and an energy storage unit configured to be connected to the DC side of the DC/AC converter. The processing circuitry 3 may be configured to control the DC/AC converter to modulate the current applied to the transmitter 9 to encode the medicament administration-related data. The trigger member 7 may when actuated/triggered cause the energy storage unit to power the processing circuitry 3 to control the DC/AC converter to modulate the current to thereby cause modulation of the current applied to the transmitter 9.

The energy storage unit may for example be a battery or a capacitor. In the latter case, the self-administrative medicament device 1 may be designed to harvest energy to thereby store energy in the capacitor. The energy harvesting may for example be obtained by removing a cap from the main body of the self-administrative medicament device 1, by movement of a movable part such as a delivery member cover, or by movement of the entire self-administration medicament device 1 by converting kinetic energy generated by the movement, and storing the energy in the capacitor.

The medicament administration-related data may for example include one of a timestamp of medicament administration, drug identification, self-administrative medicament device identification, i.e. a device ID, and drug status such as temperature range being exceeded.

The processing circuitry 3 uses any combination of one or more of a suitable central processing unit (CPU), multiprocessor, microcontroller, digital signal processor (DSP), application specific integrated circuit (ASIC), field programmable gate arrays (FPGA) etc., capable of executing any herein disclosed operations.

The self-administrative medicament device 1 may also comprise a storage medium 13 configured to store computer-executable components which when executed by the processing circuitry 3 causes the processing circuitry to modulate current generated by the power supply system 11 to be supplied to the transmitter 9 to encode the medicament administration-related data in the current to be transmitted by the transmitter 9 through the human body.

The storage medium 13 may for example be embodied as a memory, such as a random access memory (RAM), a read-only memory (ROM), an erasable programmable read-only memory (EPROM), or an electrically erasable programmable read-only memory (EEPROM) and more particularly as a non-volatile storage medium of a device in an external memory such as a USB (Universal Serial Bus) memory or a Flash memory, such as a compact Flash memory.

The processing circuitry 3, the trigger member 7, the transmitter 9 provided with a first electrode, the power supply system 11, as well as the storage medium 13 form a communications system 2. The communications system 2 may be contained within the housing of the self-administrative medicament device 1. Alternatively they may be contained in an add-on device configured to be mounted to the main body of the self-administrative medicament device, which when mounted thereto also forms part of the self-administrative medicament device 1.

The first electrode of the transmitter 9 is configured to be capacitively, galvanically, or inductively coupled to a user's skin. In this manner, the modulated current may be transmitted through the skin or body of a user when the first electrode is in direct contact with the user's skin/body.

Figure 2:
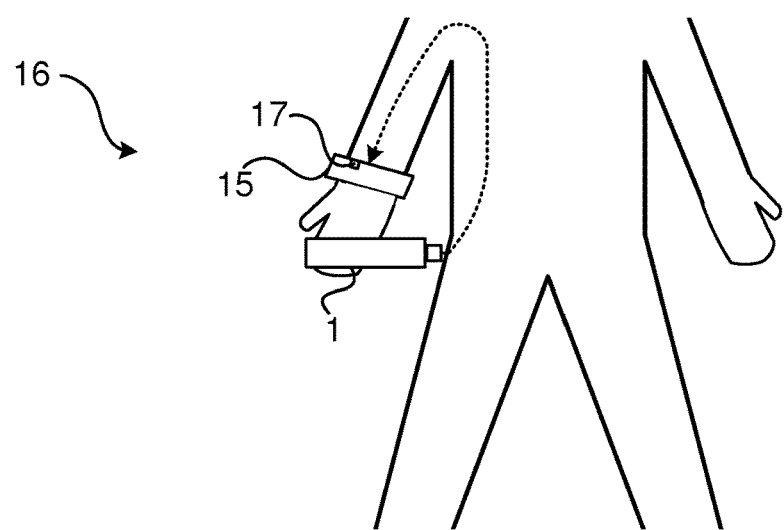
FIG. 2 shows an example of use of a self-administrative medicament device in FIG. 1 in case the self-administrative medicament device is an injector.

As shown in FIG. 2, the self-administrative medicament device 1 may be used together with a portable or mobile device 15, which together with the self-administrative medicament device 1 forms a medical system 16. The portable device 15 may for example be a smart phone, or a wearable device such as a smart phone or smart wristband, provided with a receiver 17 having a second electrode configured to be coupled to a user's skin capacitively, galvanically or inductively. The medicament administration-related data may thus be transmitted from the transmitter 13 of the self-administrative medicament device 1 to the receiver 17, through the human body. In this manner secure transmission of the medicament administration-related data may be provided through a PAN which includes a transmission medium defined by the human body. In addition, the medicament administration-related data is only transmitted when the trigger member triggers 7 the power supply system 11 to apply a current to the transmitter 9. In this manner, time-related data such as a timestamp associated with the medicament administration procedure of the self-administrative medicament device 1 may be transmitted.

The medicament administration-related data received by the receiver 17 may according to one variation be sent e.g. wirelessly through for instance a Wide Area Network (WAN) or Local Area Network (LAN) from the portable device 15 to for example a healthcare provider for example for reasons of compliance/adherence monitoring. Hereto, the portable device 15 may be configured to communicate with an external device, such as a smart phone, a computer, or an external server, using for example Bluetooth, IEEE802.11, or using cellular network communication such as GSM, UMTS and LTE and LTE Advanced.

The communication system described above may be implemented in a plurality of different self-administrative medicament devices, a few of which will be described in the following.

Figure 3:
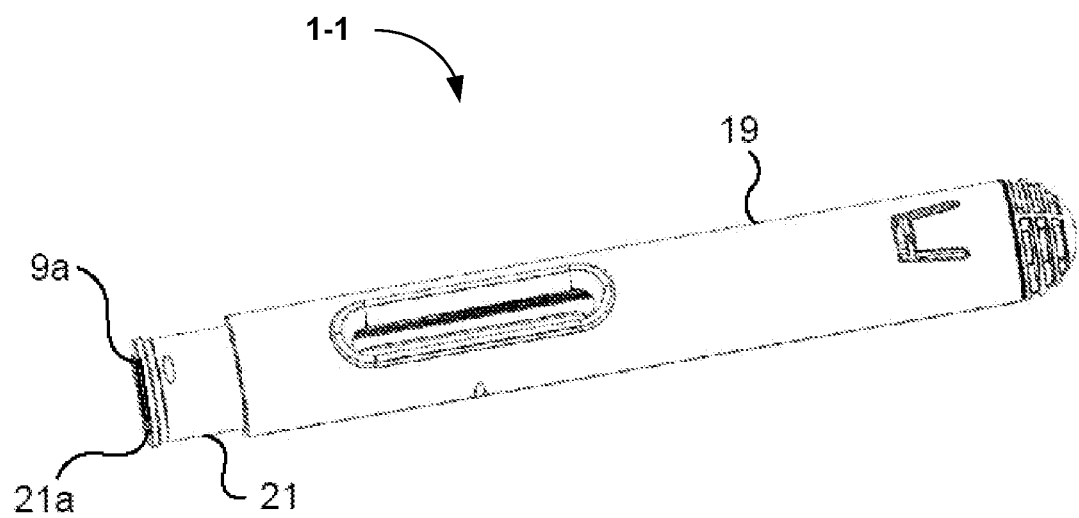
FIG. 3 shows a perspective view of an example of the self-administrative medicament device in FIG. 1 in the form of an injector.

FIG. 3 depicts an example of a self-administrative device 1-1, in the form of an injector, in particular an auto-injector. The self-administrative device 1-1 comprises a housing 19, a proximally biased linearly movable delivery member cover 21, and the communications system 2. The communications system 2 may be provided inside the housing 19 or in an add-on device configured to be mounted to a distal end of the main body of the self-administrative device 1-1, or mounted to any other position on the main body.

According to the present example, the housing 19 is configured to receive the delivery member cover 21. The delivery member cover 21 is configured to extend proximally from the housing 19, through a proximal opening of the housing 19. The delivery member cover 21 is configured to be linearly displaced relative to the housing 19, from an extended position shown in FIG. 3 to a retracted position in which the housing 19 receives a greater portion of the delivery member cover 21 compared to when in the extended position.

According to one variation of the self-administrative device 1-1, the first electrode 9a of the transmitter 7 is provided on a proximal end surface 21a of the delivery member cover 21. Thus, when the delivery member cover 21 is placed onto the injection site the first electrode 9a will be in direct contact with the subject's skin, allowing a current as modulated by the processing circuitry 3 to be transmitted through the subject's body.

Alternatively, the first electrode 9a of the transmitter 9 may be provided on the delivery member/needle (not shown).

When the delivery member cover 21 is placed onto the injection site and the first electrode 9a is brought into contact with the skin, and the housing 19 is pressed towards the injection site, the delivery member cover 21 will be pressed into the housing 19. In this manner, the trigger member 7 may be actuated either by direct cooperation with the delivery member cover 21 or by cooperation with another movable member, contained in the self-administrative medicament device 1-1, which has been set into motion as a result of the delivery member cover 21 being moved from the extended position towards the retracted position. The power supply system 11 is thereby triggered to apply a current to the first electrode 9a, and the processing circuitry is thus configured to modulate the current to be transmitted by the transmitter 9 via the first electrode 9a.

Figure 4:
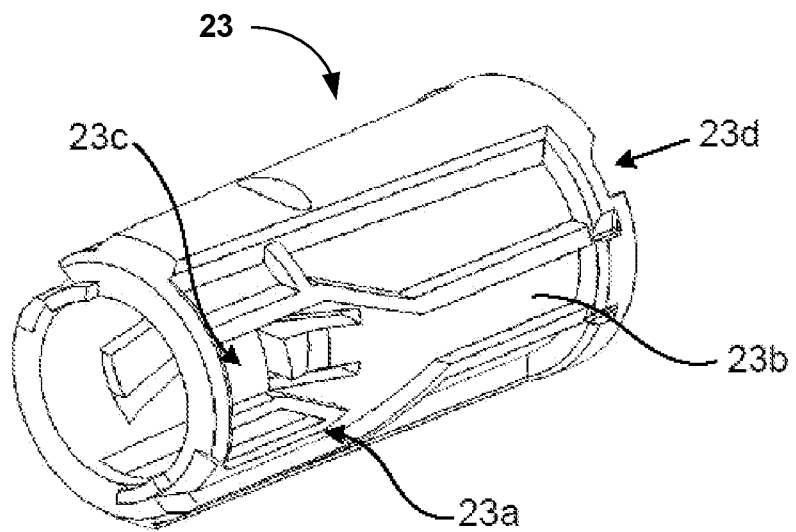
FIG. 4 shows a perspective view of an example of a movable sleeve of the self-administrative medicament device in FIG. 3.

An example of another movable member that may be configured to actuate the trigger member 7 will now be described with reference to FIG. 4. The self-administrative medicament device 1-1- may comprise a movable sleeve 23, or rotator, configured to be arranged in the housing 19 and configured to cooperate directly with the delivery member cover 21. The movable sleeve 23 comprises a plurality of grooves 23a-c extending in the axial direction along the outer surface of the movable sleeve 23. The delivery member cover 21 has a radially inwards extending protrusion provided at a distal end thereof, configured to be received in the grooves 23a-c to enable cooperation between the delivery member cover 21 and the movable sleeve 23. In this manner, linear displacement of the delivery member cover 21 from the extended position causes rotation of the movable sleeve 23 and the radially inwards extending protrusion will be moved from groove 23a into groove 23b via an inclined surface. When the delivery member cover 21 is moved back towards the extended position, due to the proximal biasing, the radially inwards extending protrusion will slide into groove 23c, which includes a blocking feature that prevents the delivery member cover 21 from being moved back towards the retracted position once the delivery member cover 21 has returned to the extended position.

The movable sleeve 23 may be provided with one or more distal recesses 23d. The self-administrative medicament device 1-1 may comprise a proximally biased rod, not shown, configured to be in direct contact with the distal end face of the movable sleeve 23, and to move into a distal recess 23d, when the movable sleeve 23 is being rotated when cooperating with the delivery member cover 21. The rod, which is able to move in the axial direction when moving in and out from the distal recess 23d may be configured to actuate the trigger member 7, causing the trigger member 7 to trigger the power supply system 11 to apply a current to the transmitter 9 and to the processing circuitry 3, to enable modulation of the current to be transmitted via the first electrode 9a. The rod which is configured to interact with the movable sleeve 23 is hence another example of a movable member.

The trigger member 7 may in the above variation for example be a mechanical switch.

Figure 5:
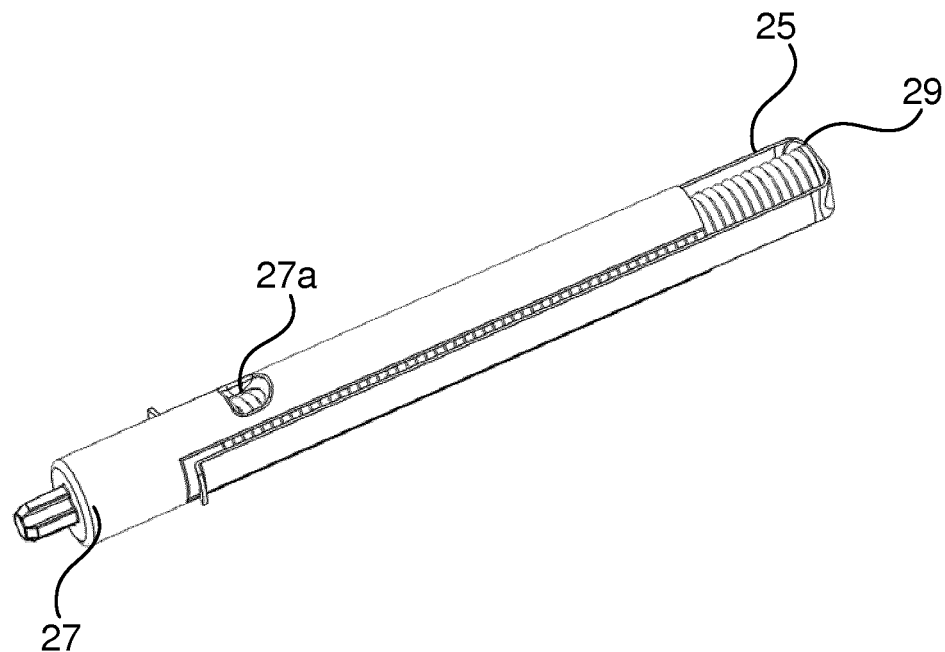
FIG. 5 shows a perspective view of an example of a plunger rod and U-shaped bracket.
Figure 6:
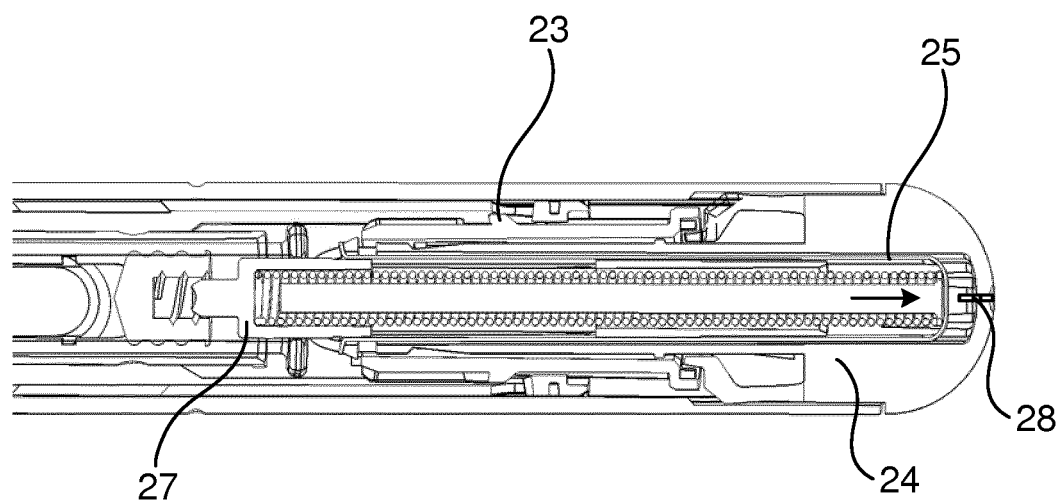
FIG. 6 is a longitudinal section of a distal end portion of the self-administrative medicament device shown in FIG. 3.

Another example of a movable member that may be configured to actuate the trigger member 7 is shown in FIG. 5. According to this variation, the self-administrative medicament device 1-1 includes a tubular extension member 24 provided with radially flexible arms, a signal generating member, for example a U-shaped bracket 25 provided with two longitudinally extending legs, configured to be received by the tubular extension member and a plunger rod 27 configured to be received between the legs of the U-shaped bracket 25. Also in this example, the self-administrative medicament device 1-1 comprises a movable sleeve such as movable sleeve 23. The movable sleeve is configured to receive the tubular extension member 24, and the radially flexible arms are configured to be pressed radially inwards by the inner surface of the movable sleeve. The plunger rod 27, which has radial recesses 27a configured to receive a respective one of the radially flexible arms therein, is thereby maintained in an initial axial position. The movable sleeve furthermore has an inner surface provided with recesses. When the movable sleeve is being rotated, the radially flexible arms, which initially are pressed radially inwards by the inner surface of the movable sleeve, will be able to flex radially outwards, into the recesses of the movable sleeve. The plunger rod 27 is thereby released from its axially fixed position. The self-administrative medicament device 1-1 also includes a resilient member 29, configured to bias the U-shaped bracket 25 in the distal direction, and a movable rod 28 provided distally from and axially aligned with the U-shaped bracket, as shown in FIG. 6. When the plunger rod 27 is released and moved in the proximal direction, the resilient member 29 will cause the U-shaped bracket 25 to be thrown backwards as indicated by the arrow in FIG. 6, i.e. in the distal direction towards the movable rod 28, which may be configured to actuate the trigger member 7. The movable member may thus in this case be the movable rod 28. Alternatively, there may be no movable rod provided and U-shaped bracket 25 may be configured to directly contact the trigger member 7, in which case the movable member configured to actuate the trigger member 7 is the U-shaped bracket 25.

According to another variation, the self-administrative medicament device may be a button-activated injector. In this case, the button which initiates medicament administration may be configured to actuate the trigger member 7, for example in the form of a mechanical switch.

Figure 7:
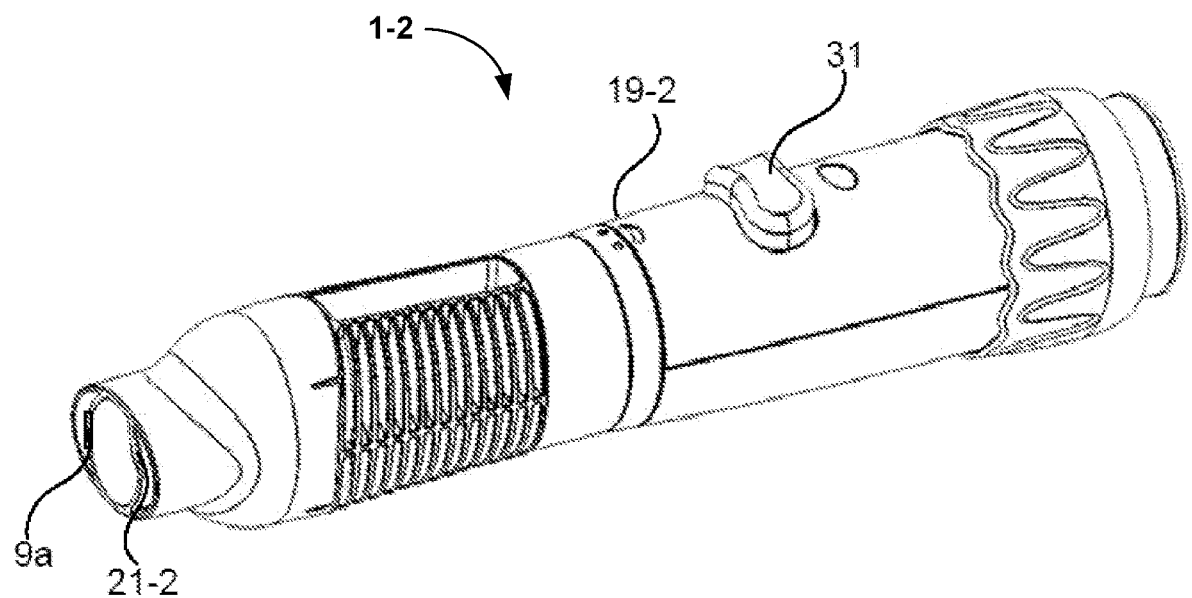
FIG. 7 shows a perspective view of yet another example of a self-administrative medicament device, in the form of an inhaler.

FIG. 7 shows another example of a self-administrative medicament device. Self-administrative medicament device 1-2 is an inhaler comprising a housing 19-2 configured to receive a medicament container assembly including a medicament container and a delivery member, and the communications system 2. The delivery member is in this case a nozzle. The exemplified self-administrative medicament device 1-2 is button-activated, and has a button 31 for initiating medicament administration.

The communications system 2 may be integrated with the main body of the self-administrative medicament device 1-2, or it may be provided as an add-on device which is configured to be mounted to the main body. In variations in which the communications system is included in the main body of the self-administrative medicament device 1-2 the button 31 may be configured to actuate the trigger member 7 to trigger the power supply system 11 and the processing circuitry 3.

The self-administrative medicament device 1-2 furthermore includes a delivery member cover 21-2 configured to be in contact with a user's body when in use. The delivery member cover 21-2 has a proximal end portion which according to one variation may be provided with the first electrode 9a configured to be coupled to a user's skin or body.

Figure 8:
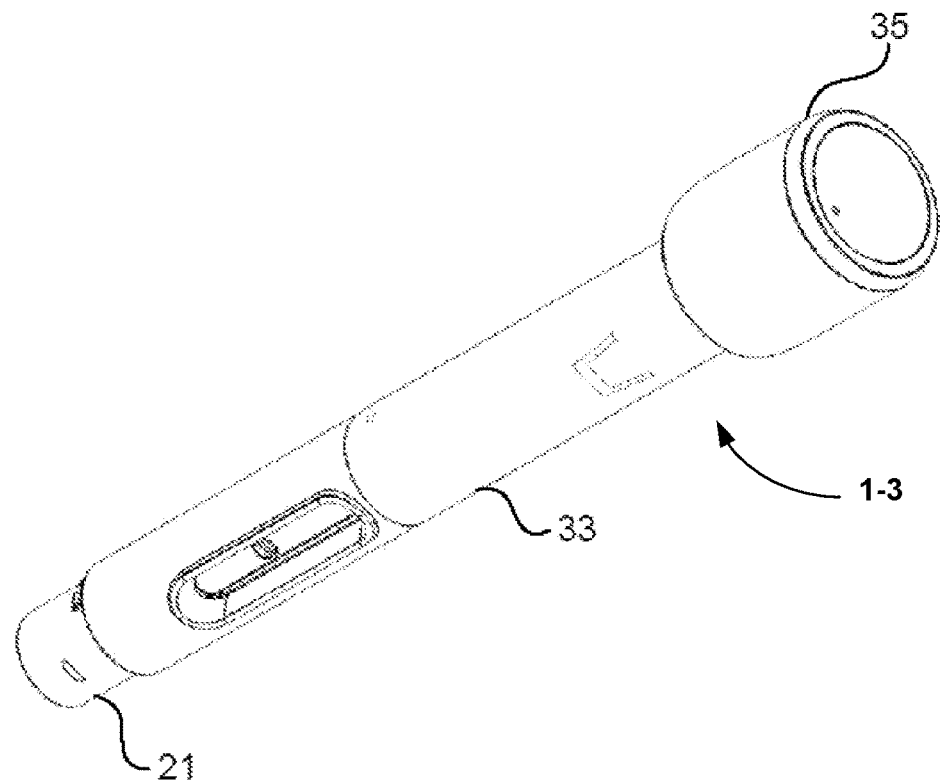
FIG. 8 shows a perspective view of an example of a self-administrative medicament device including an add-on device mounted to a distal end portion of a main body of the self-administrative medicament device.

With reference to FIG. 8, an example of a self-administrative medicament device 1-3 is shown. Self-administrative medicament device 1-3 has a main body 33, and an add-on device 35 mounted to a distal end portion of the main body 33. According to this example, the add-on device 35 includes a majority of, or all the components of the communications system 2.

Figure 9:
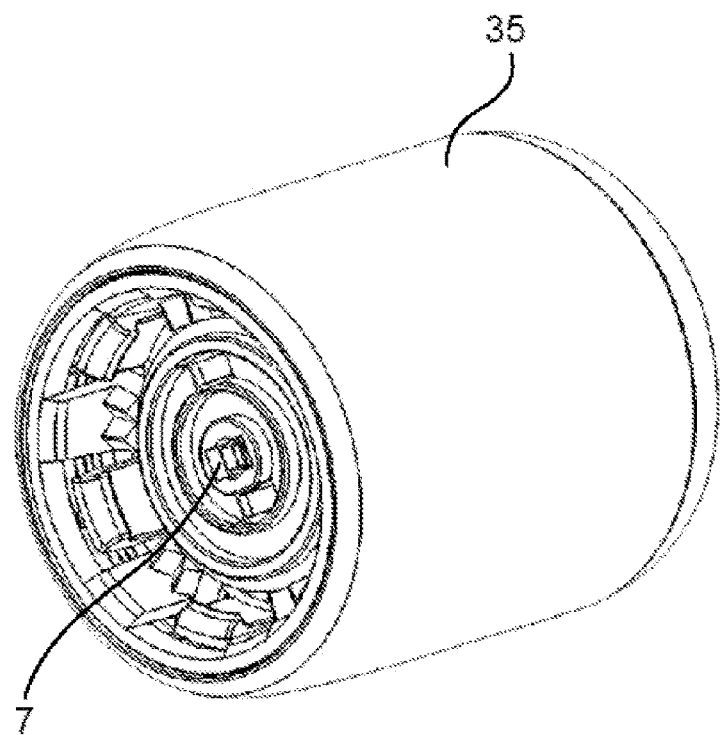
FIG. 9 shows a perspective view of an example of the add-on device shown in FIG. 8.

Although the main body is provided with the first electrode, for example on the proximal end surface of the delivery member cover, an electrode in the form of an electrical connection to be connected to the first electrode must also be provided in the add-on device 35, at the interface configured to be connected to the main body 33. This electrode of the add-on device 35 may in this sense be seen as the first electrode or forming part of the first electrode, as it is at least indirectly configured to be coupled to a user's skin. The trigger member 7 may for example be provided centred at a proximal end of the add-on device 35, as shown in FIG. 9, for example for cooperation with the previously described U-shaped bracket or movable rod 28.

Figure 10:
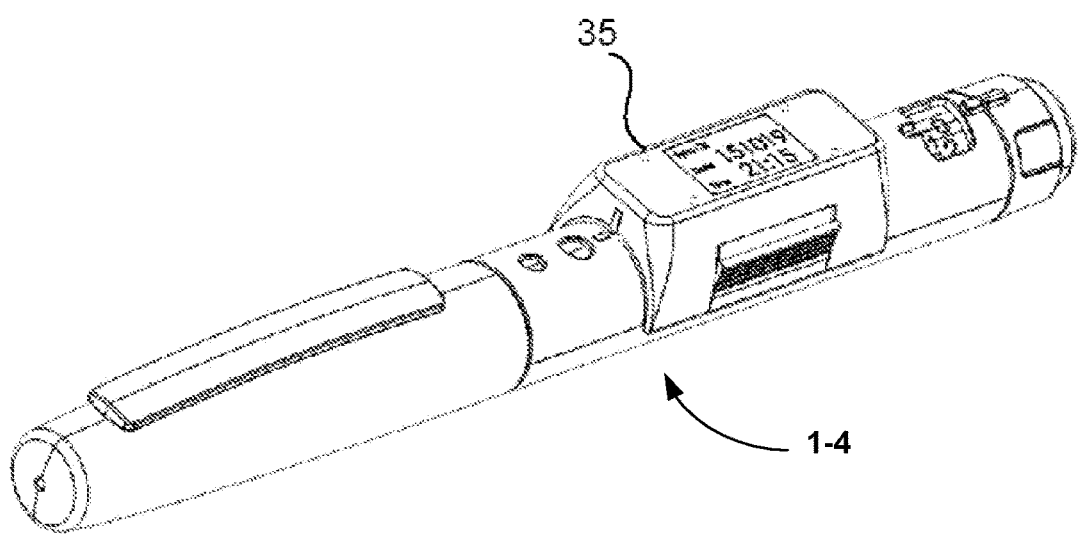
FIG. 10 shows a perspective view of another example of a self-administrative medicament device provided with an example of an add-on device.

FIG. 10 shows yet another example of a self-administrative medicament device 1-4, in the form of a pen device, provided with an add-on device 35. As previously described, the communications system 2 may be included in the add-on device 35 or in the main body of the self-administrative medicament device 1-4.

According to any example disclosed herein, the self-administrative medicament device may include a receiver having a second electrode, configured to be coupled to the skin of a user. The receiver may be configured to receive medicament administration-related data transmitted through the human body from the transmitter. In this case, the self-administrative medicament device may also include a wireless transmitter, an antenna, configured to transmit received medicament administration-related data wirelessly from the self-administrative medicament device to an external receiver, e.g. a mobile phone, a computer, or a remote device using for example Bluetooth, IEEE802.11, or using cellular network communication such as GSM, UMTS and LTE and LTE Advanced. Such a variation may especially be advantageous in case the self-administrative medicament device is an injector and the delivery member, a needle, defines the first electrode. In this case, medicament administration-related data is sent through the body only when the needle has been inserted into the body, and reception of medicament administration-related data to be transmitted by the antenna may facilitate compliance requirements.

Skin has an irregular surface structure, and there may be bodily hair present which reduces the strength of the coupling in case of a single first electrode. Hence, according to any example disclosed herein, the self-administrative medicament device may comprise one or more electrode members forming the first electrode 9a and one or more electrode members forming the second electrode. In this way better coupling to the user's skin/body may be provided. There may for example be provided several electrode members forming the first electrode along the circumference of the proximal end surface of the delivery member cover to ensure better contact with the user's skin.

The inventive concept has mainly been described above with reference to a few examples. However, as is readily appreciated by a person skilled in the art, other embodiments than the ones disclosed above are equally possible within the scope of the inventive concept, as defined by the appended claims.

The invention claimed is:

1. A self-administrative medicament device comprising: processing circuitry,
a transmitter having a first electrode configured to be coupled to a user's skin only during a medicament expulsion procedure,
a power supply system configured to apply a current to the transmitter,
a trigger member configured to trigger the power supply system to apply the current to the transmitter,
a housing,
a delivery member cover that extends proximally from the housing through a proximal opening of the housing, and
a movable sleeve positioned in the housing and configured to cooperate directly with the delivery member cover,
wherein the processing circuitry is configured to modulate the current generated by the power supply system to encode medicament administration-related data to be transmitted through the user's skin by the transmitter via the first electrode,
wherein the delivery member cover is configured to be linearly displaced relative to the housing from an extended position to a retracted position during the medicament expulsion procedure,
wherein the housing receives a greater portion of the delivery member cover in the retracted position compared to the extended position,
wherein the trigger member is configured to trigger the power supply system to apply the current to the transmitter by movement of the delivery member cover from the extended position to the retracted position, which movement only occurs during the medicament expulsion procedure,
wherein the first electrode is provided on a proximal end surface of the delivery member cover that is configured to contact the user's skin during the medicament expulsion procedure,
wherein the movable sleeve comprises a plurality of grooves extending in an axial direction along an outer surface of the movable sleeve, and
wherein the delivery member cover has a radially inwards extending protrusion provided at a distal end thereof, configured to be received in the plurality of grooves to enable cooperation between the delivery member cover and the movable sleeve.

2. The self-administrative medicament device as claimed in claim 1,
wherein the trigger member comprises a mechanical switch configured to be actuated by the delivery member cover when the delivery member cover is axially displaced from the extended position towards the retracted position.

3. The self-administrative medicament device as claimed in claim 1,
wherein the power supply system includes an energy storage unit and a DC/AC converter.

4. The self-administrative medicament device as claimed in claim 3,
wherein the processing circuitry is configured to control the DC/AC converter to modulate the current to encode the medicament administration-related data.

5. The self-administrative medicament device as claimed in claim 1, further comprising
a receiver of a portable device having an electrode configured to be coupled to the user's skin, wherein the receiver is configured to receive the medicament administration-related data transmitted by the transmitter via the user's skin.

6. The self-administrative medicament device as claimed in claim 1,
wherein the medicament administration-related data includes at least one of a timestamp of medicament administration, drug identification, self-administrative medicament device identification, and drug status.

7. The self-administrative medicament device as claimed in claim 1, wherein the self-administrative medicament device comprises an injector or an inhaler.

8. A medical system comprising:
the self-administrative medicament device of claim 1, and
a portable device comprising a receiver having an electrode configured to be coupled to the user's skin.

9. The medical system as claimed in claim 8,
wherein the self-administrative medicament device is configured to transmit the medicament administration-related data via the transmitter to the receiver.

10. The medical system as claimed in claim 8, wherein the portable device comprises a wearable device.

11. The medical system as claimed in claim 8, wherein the portable device comprises a smart phone.

12. The medical system as claimed in claim 10, wherein the wearable device comprises a smart watch.

13. The medical system as claimed in claim 10, wherein the wearable device comprises a smart wrist band.

14. The self-administrative medicament device as claimed in claim 1,
wherein linear displacement of the delivery member cover from the extended position causes rotation of the movable sleeve and the radially inwards extending protrusion will be moved from a first groove of the plurality of grooves to a second groove of the plurality of grooves via an inclined surface.

15. The self-administrative medicament device as claimed in claim 14,
wherein when the delivery member cover is moved back towards the extended position, due to a proximal biasing, the radially inwards extending protrusion will slide into a third groove of the plurality of grooves which includes a blocking feature that prevents the delivery member cover from being moved back towards the retracted position once the delivery member cover has returned to the extended position.

* * * * *